United States Patent
Kim et al.

(10) Patent No.: US 10,245,127 B2
(45) Date of Patent: Apr. 2, 2019

(54) METHOD OF MANUFACTURING MULTILAYER ZIRCONIA BLOCK FOR ARTIFICIAL TEETH

(71) Applicant: DENTAL MAX CO., LTD., Seoul (KR)

(72) Inventors: Jin Dong Kim, Chungcheongnam-do (KR); Seung Bum Park, Chungcheongnam-do (KR)

(73) Assignee: DENTAL MAX CO., LTD., Seoul (KR)

( * ) Notice: Subject to any disclaimer, the term of this patent is extended or adjusted under 35 U.S.C. 154(b) by 197 days.

(21) Appl. No.: 15/237,962

(22) Filed: Aug. 16, 2016

(65) Prior Publication Data

US 2016/0354186 A1    Dec. 8, 2016

Related U.S. Application Data

(63) Continuation of application No. PCT/KR2015/008606, filed on Aug. 18, 2015.

(30) Foreign Application Priority Data

Mar. 19, 2015   (KR) .......................... 10-2015-0038314

(51) Int. Cl.
*A61C 13/083* (2006.01)
*A61C 13/09* (2006.01)
(Continued)

(52) U.S. Cl.
CPC .......... *A61C 13/09* (2013.01); *A61C 13/0022* (2013.01); *A61C 13/081* (2013.01);
(Continued)

(58) Field of Classification Search
None
See application file for complete search history.

(56) References Cited

U.S. PATENT DOCUMENTS 9,212,065 B2 *  12/2015  Yamada ................. C01G 25/02
9,687,325 B2 *   6/2017  Park ..................... A61C 13/0022
(Continued)

FOREIGN PATENT DOCUMENTS

KR    10-2011-0112740 A    10/2011
KR      10-1221026 B1     1/2013
(Continued)

OTHER PUBLICATIONS

Derwent abstract of Chinese reference CN 1132730 A dated Oct. 9, 1996. (Year: 1996).*

*Primary Examiner* — Robert B Davis
(74) *Attorney, Agent, or Firm* — Mintz Levin Cohn Ferris Glovksy and Popeo, P.C.; Kongsik Kim; Jhongwoo Jay Peck

(57) ABSTRACT

Disclosed is a method of manufacturing a multilayer zirconia block for artificial teeth, including a first material mixing step of mixing a 3 mol % yttrium oxide-tetragonal zirconia polycrystal and an organic binder, a second material mixing step of mixing a 3 mol % yttrium oxide-tetragonal zirconia polycrystal, a 5 mol % yttrium oxide-tetragonal zirconia polycrystal and an organic binder, a third material mixing step of mixing a 5 mol % yttrium oxide-tetragonal zirconia polycrystal and an organic binder, a compression molding step of sequentially placing the mixtures obtained in the first material mixing step, the second material mixing step, and the third material mixing step in a mold for compression molding and performing compression molding, and a calcination step of calcining a compression molded product obtained in the compression molding step. This method provides a multilayer zirconia block that contains yttrium oxide, the amount of which is adjusted in the manufacturing process, thus showing a color similar to that of natural teeth after impregnation with a coloring solution.

9 Claims, 1 Drawing Sheet

(51) Int. Cl.
| | |
|---|---|
| *B32B 18/00* | (2006.01) |
| *A61C 13/20* | (2006.01) |
| *A61C 13/00* | (2006.01) |
| *A61C 13/08* | (2006.01) |
| *A61K 6/04* | (2006.01) |
| *A61K 6/05* | (2006.01) |
| *A61K 6/083* | (2006.01) |
| *A61K 6/087* | (2006.01) |
| *B28B 3/00* | (2006.01) |
| *B32B 5/16* | (2006.01) |
| *C04B 35/48* | (2006.01) |
| *C04B 35/634* | (2006.01) |
| *C04B 35/638* | (2006.01) |
| *A61K 6/02* | (2006.01) |
| *C04B 35/486* | (2006.01) |

(52) U.S. Cl.
CPC ............ *A61C 13/083* (2013.01); *A61C 13/20* (2013.01); *A61K 6/024* (2013.01); *A61K 6/043* (2013.01); *A61K 6/05* (2013.01); *A61K 6/083* (2013.01); *A61K 6/087* (2013.01); *B28B 3/00* (2013.01); *B32B 5/16* (2013.01); *B32B 18/00* (2013.01); *C04B 35/48* (2013.01); *C04B 35/486* (2013.01); *C04B 35/638* (2013.01); *C04B 35/63416* (2013.01); *C04B 35/63444* (2013.01); *C04B 35/63488* (2013.01); *B32B 2250/03* (2013.01); *B32B 2260/025* (2013.01); *B32B 2260/046* (2013.01); *B32B 2264/107* (2013.01); *B32B 2307/402* (2013.01); *B32B 2535/00* (2013.01); *C04B 2235/3224* (2013.01); *C04B 2235/3225* (2013.01); *C04B 2235/3246* (2013.01); *C04B 2235/3272* (2013.01); *C04B 2235/3275* (2013.01); *C04B 2235/3281* (2013.01); *C04B 2235/444* (2013.01); *C04B 2235/602* (2013.01); *C04B 2235/656* (2013.01); *C04B 2235/9661* (2013.01); *C04B 2237/348* (2013.01); *C04B 2237/58* (2013.01)

(56) References Cited

U.S. PATENT DOCUMENTS

| | | | |
|---|---|---|---|
| 2006/0008774 A1* | 1/2006 | Orth | A61C 13/0004 433/202.1 |
| 2007/0292597 A1* | 12/2007 | Ritzberger | A61C 13/0022 427/2.29 |
| 2009/0092531 A1* | 4/2009 | Katusic | B82Y 30/00 423/263 |
| 2009/0321971 A1* | 12/2009 | Brodkin | A61C 13/0006 264/17 |
| 2010/0003630 A1* | 1/2010 | Yamashita | B82Y 30/00 433/8 |
| 2010/0216095 A1* | 8/2010 | Scharf | A61C 13/083 433/212.1 |
| 2012/0196244 A1* | 8/2012 | Khan | A61C 13/082 433/6 |
| 2012/0231417 A1* | 9/2012 | Stephan | A61C 8/0012 433/172 |
| 2013/0221554 A1 | 8/2013 | Jung et al. | |

FOREIGN PATENT DOCUMENTS

| | | |
|---|---|---|
| KR | 10-1276616 B1 | 6/2013 |
| KR | 10-1324467 B1 | 11/2013 |

* cited by examiner

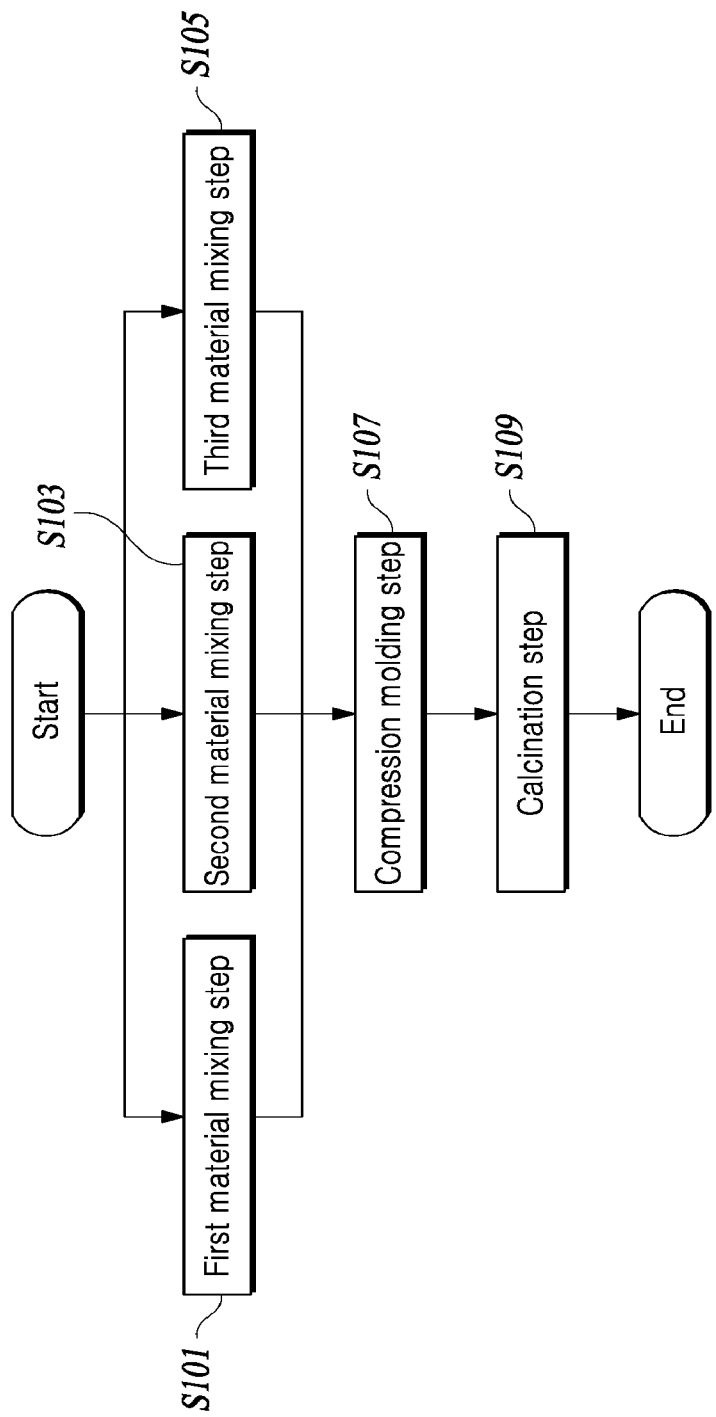

METHOD OF MANUFACTURING MULTILAYER ZIRCONIA BLOCK FOR ARTIFICIAL TEETH

CROSS-REFERENCE TO RELATED APPLICATIONS

This is a continuation application of International Application No. PCT/KR2015/008606 filed on Aug. 18, 2015, which claims priority to Korean Application No. 10-2015-0038314 filed on Mar. 19, 2015, which applications are incorporated herein by reference.

TECHNICAL FIELD

The present invention relates to a method of manufacturing a multilayer zirconia block for artificial teeth and, more particularly, to a method of manufacturing a multilayer zirconia block for artificial teeth, in which the multilayer zirconia block contains yttrium oxide, the amount of which is adjusted in the manufacturing process, thus showing a color similar to that of natural teeth after impregnation with a coloring solution.

BACKGROUND ART

For replacement with an artificial tooth via dental diagnosis in a dental clinic, the shape of the original tooth is typically captured by the dentist and then delivered to a dental laboratory. More specifically, the tooth model is formed based on the shape of the original tooth in the dental laboratory, scanned and imaged, and such an image is input to a computer, after which a block for molding an artificial tooth is fixed and processed using a small CNC (CAD/CAM) device, as a processing device, and then the processed tooth is heat treated, thus yielding an artificial tooth.

As for the processing device, such as a CNC device, a transfer table having a drill fixed thereto is moved upward/downward and leftward/rightward in accordance with the image input to the computer so that the block for molding an artificial tooth is processed. In this case, the block is processed to be larger than the actual tooth size and reduced in a heat treatment process. The artificial tooth thus completed is delivered again to the dental clinic and thus applied to the corresponding patient.

However, the block for molding an artificial tooth, which is conventionally manufactured, shows a color that is not similar to that of the natural tooth adjacent thereto after impregnation with the coloring solution, and thus, the artificial tooth is visibly distinguishable from the other teeth after application, undesirably causing a poor outer appearance.

In general, natural teeth are not completely white, with a dark yellow color at the root portion of the tooth and a degree of whiteness increasing with increasing distance from the root portion. Since individual patients have varying tooth colors, what is required is a block for molding an artificial tooth that shows a color similar to that of the natural teeth of the corresponding patient after impregnation with the coloring solution.

SUMMARY

Accordingly, the present invention is intended to provide a method of manufacturing a multilayer zirconia block for artificial teeth, in which the multilayer zirconia block contains yttrium oxide, the amount of which is adjusted in the manufacturing process, thus showing a color similar to that of natural teeth.

The present invention provides a method of manufacturing a multilayer zirconia block for artificial teeth, comprising: a first material mixing step of mixing a 3 mol % yttrium oxide-tetragonal zirconia polycrystal and an organic binder, a second material mixing step of mixing a 3 mol % yttrium oxide-tetragonal zirconia polycrystal, a 5 mol % yttrium oxide-tetragonal zirconia polycrystal and an organic binder, a third material mixing step of mixing a 5 mol % yttrium oxide-tetragonal zirconia polycrystal and an organic binder, a compression molding step of sequentially placing mixtures, obtained in the first material mixing step, the second material mixing step, and the third material mixing step, in a mold for compression molding and performing compression molding, and a calcination step of calcining a compression molded product obtained in the compression molding step.

Preferably, the first material mixing step comprises mixing 93 to 99.9 wt % of the 3 mol % yttrium oxide-tetragonal zirconia polycrystal and 0.1 to 7 wt % of the organic binder.

More preferably, the second material mixing step comprises mixing 10 to 90 wt % of the 3 mol % yttrium oxide-tetragonal zirconia polycrystal, 3 to 89.9 wt % of the 5 mol % yttrium oxide-tetragonal zirconia polycrystal, and 0.1 to 7 wt % of the organic binder.

Even more preferably, the third material mixing step comprises mixing 93 to 99.9 wt % of the 5 mol % yttrium oxide-tetragonal zirconia polycrystal and 0.1 to 7 wt % of the organic binder.

Still more preferably, the calcination step comprises placing the compression molded product, obtained in the compression molding step, in an electric furnace and heating the compression molded product to a temperature of 850 to 1050° C.

Yet more preferably, the organic binder comprises any one selected from the group consisting of polyvinyl alcohol, polyvinyl pyrrolidine, and polyethylene glycol.

According to the present invention, the method of manufacturing a multilayer zirconia block for artificial teeth is very effective at providing a multilayer zirconia block that contains yttrium oxide, the amount of which is adjusted in the manufacturing process, thus showing a color similar to that of natural teeth after impregnation with a coloring solution.

BRIEF DESCRIPTION OF DRAWINGS

FIG. 1 is a flowchart illustrating the process of manufacturing a multilayer zirconia block for artificial teeth according to the present invention.

DETAILED DESCRIPTION

Hereinafter, preferred embodiments of the present invention and properties of individual components are described in detail so that the invention may be easily performed by those skilled in the art to which the present invention belongs, but are not to be construed as limiting the spirit and scope of the present invention.

The present invention addresses a method of manufacturing a multilayer zirconia block for artificial teeth, comprising: a first material mixing step (S101) of mixing a 3 mol % yttrium oxide-tetragonal zirconia polycrystal and an organic binder, a second material mixing step (S103) of mixing a 3 mol % yttrium oxide-tetragonal zirconia polycrystal, a 5 mol % yttrium oxide-tetragonal zirconia polycrystal and an organic binder, a third material mixing step (S105) of mixing a 5 mol % yttrium oxide-tetragonal zirconia polycrystal and an organic binder, a compression molding step (S107) of sequentially placing mixtures, obtained in the first material mixing step (S101), the second material mixing step (S103), and the third material mixing step (S105), in a mold for compression molding and performing compression molding, and a calcination step (S109) of calcining a compression molded product obtained in the compression molding step (S107).

In the first material mixing step (S101) of mixing a 3 mol % yttrium oxide-tetragonal zirconia polycrystal and an organic binder, 93 to 99.9 wt % of the 3 mol % yttrium oxide-tetragonal zirconia polycrystal and 0.1 to 7 wt % of the organic binder are mixed.

The organic binder is used in an amount of 0.1 to 7 wt %, and functions to bind the 3 mol % yttrium oxide-tetragonal zirconia polycrystal and also to bind the mixtures upon compression molding in the mold for compression molding, into which the mixtures prepared in the first material mixing step, the second material mixing step, and the third material mixing step are sequentially placed in the compression molding step.

If the amount of the organic binder is less than 0.1 wt %, the ability to bind the 3 mol % yttrium oxide-tetragonal zirconia polycrystal may decrease. On the other hand, if the amount thereof exceeds 7 wt %, the relative amount of the 3 mol % yttrium oxide-tetragonal zirconia polycrystal may be reduced, undesirably deteriorating the mechanical properties of the multilayer zirconia block for artificial teeth.

The organic binder preferably includes any one selected from the group consisting of polyvinyl alcohol, polyvinyl pyrrolidine, and polyethylene glycol, and the organic binder composed of the above component functions to further enhance the mechanical strength of artificial teeth.

In the second material mixing step (S103) of mixing a 3 mol % yttrium oxide-tetragonal zirconia polycrystal, a 5 mol % yttrium oxide-tetragonal zirconia polycrystal and an organic binder, 10 to 90 wt % of the 3 mol % yttrium oxide-tetragonal zirconia polycrystal, 3 to 89.9 wt % of the 5 mol % yttrium oxide-tetragonal zirconia polycrystal, and 0.1 to 7 wt % of the organic binder are mixed.

The present invention takes advantage of variation in the whiteness index of a yellow color depending on the extent of the reaction of the 3 mol % yttrium oxide-tetragonal zirconia polycrystal and the 5 mol % yttrium oxide-tetragonal zirconia polycrystal with the component of the coloring solution. Specifically, when comparing the 5 mol % yttrium oxide-tetragonal zirconia polycrystal with the 3 mol % yttrium oxide-tetragonal zirconia polycrystal, the whiteness index is higher even upon immersion in the coloring solution comprising the same component for the same time. This is because the whiteness index is increased after sintering in proportion to the increase in the amount of yttrium oxide when yttrium oxide ($Y_2O_3$), contained in the above two materials, reacts in the sintering process with the main component of the coloring solution used to realize a color similar to that of natural teeth, for example, $Fe_2O_3$, $CeO_2$, $CrO_2$, $Er_2O_3$, $MoO_3$, $MnO_2$, $BaO$, $V_2O_5$, $V_2O_3$, and $CoO$.

Furthermore, the 5 mol % yttrium oxide-tetragonal zirconia polycrystal has higher light transmittance than that of the 3 mol % yttrium oxide-tetragonal zirconia polycrystal. The ratio of the amounts of the above two materials is adjusted, and thus, a mixture containing a larger amount of 5 mol % yttrium oxide-tetragonal zirconia polycrystal may be applied from the root portion of the tooth toward the top portion thereof so as to ensure an artificial tooth similar to a natural tooth. The artificial tooth is preferably manufactured so as to have 1 to 8 regions having different whiteness indices taking into consideration the size thereof. When the above mixture is used together with the mixtures obtained in the first material mixing step (S101) and the third material mixing step (S105), 3 to 10 regions having different whiteness indices may result.

As such, the component and function of the organic binder are the same as in the description of the first material mixing step (S101), and thus a description thereof is omitted.

In the third material mixing step (S105) of mixing a 5 mol % yttrium oxide-tetragonal zirconia polycrystal and an organic binder, 93 to 99.9 wt % of the 5 mol % yttrium oxide-tetragonal zirconia polycrystal and 0.1 to 7 wt % of the organic binder are mixed.

The mixture obtained in the third material mixing step (S105) shows the brightest whiteness index because it is composed exclusively of the 5 mol % yttrium oxide-tetragonal zirconia polycrystal and the organic binder.

As such, the component and function of the organic binder are the same as in the description of the first material mixing step (S101), and thus a description thereof is omitted.

The compression molding step (S107) is performed in a manner in which the mixtures, obtained in the first material mixing step (S101), the second material mixing step (S103) and the third material mixing step (S105), are sequentially placed in the mold for compression molding and then subjected to compression molding.

The amounts of the mixtures of the first material mixing step (S101), the second material mixing step (S103) and the third material mixing step (S105), which are added into the mold for compression molding, are not particularly limited, and may be freely selected considering the tooth color or the manufacturing process, but are preferably set to a weight ratio of 1:8:1 so as to produce a compression molded product having a thickness of 10 to 30 mm.

The compression molding machine and conditions used for the compression molding step (S107) are not particularly limited so long as they are typically useful in the production of blocks for artificial teeth. By means of the organic binder contained in the mixtures obtained in the first material mixing step (S101), the second material mixing step (S103) and the third material mixing step (S105), individual mixtures are strongly bound to each other through the compression molding step (S107), resulting in a compression molded product having high mechanical strength.

Among the mixtures placed in the mold, the mixture obtained in the second material mixing step (S103) may be provided in the form of multiple layers showing 8 different whiteness indices from a single color depending on the natural tooth color of the patient receiving treatment. The whiteness index of the mixture obtained in the second material mixing step (S103) is determined by the mixing ratio of the 3 mol % yttrium oxide-tetragonal zirconia polycrystal and the 5 mol % yttrium oxide-tetragonal zirconia polycrystal.

The calcination step (S109) is performed in a manner in which the compression molded product obtained in the compression molding step (S107) is calcined. Specifically, the compression molded product obtained in the compression molding step (S107) is placed in an electric furnace and heated to a temperature of 850 to 1050° C. The calcination step (S109) enables the organic binder to be removed from the compression molded product obtained in the compression molding step (S107), resulting in a multilayer zirconia block for artificial teeth having high mechanical strength.

When the multilayer zirconia block obtained in the calcination step (S109) is colored with a coloring solution, 3 to 10 different whiteness indices may be shown. The coloring solution is mainly composed of $FeCl_3 \cdot 6H_2O$ to show a yellow color, of $Cl_3Er \cdot 6H_2O$ to show a pink color, of $COCl_2 \cdot 6H_2O$ to show a purple color, and of $CuCl_2$ to show a blue color, and thus a $FeCl_3 \cdot 6H_2O$-based coloring solution is mostly used. Distilled water is mixed with each component to control the intensity of color so as to obtain a color similar to that of the natural teeth of the patient receiving treatment.

After the calcination step (S109), the formation of the multilayer zirconia block for artificial teeth according to the present invention is completed. The multilayer zirconia block for artificial teeth can show a color similar to that of the natural teeth of the corresponding patient after impregnation with the coloring solution by adjusting the amount of yttrium oxide in the manufacturing process.

DESCRIPTION OF THE REFERENCE NUMERALS IN THE DRAWING

S101: First material mixing step
S103: Second material mixing step
S105: Third material mixing step
S107: Compression molding step
S109: Calcination step

The invention claimed is:

1. A method of manufacturing a multilayer zirconia block for artificial teeth, comprising:
   a first material mixing step of mixing a 3 mol % yttrium oxide-tetragonal zirconia polycrystal and an organic binder;
   a third material mixing step of mixing a 5 mol % yttrium oxide-tetragonal zirconia polycrystal and the organic binder;
   a second material mixing step of mixing the 3 mol % yttrium oxide-tetragonal zirconia polycrystal, the 5 mol % yttrium oxide-tetragonal zirconia polycrystal, and the organic binder, wherein the 3 mol % yttrium oxide-tetragonal zirconia polycrystal and the 5 mol % yttrium oxide-tetragonal zirconia polycrystal are mixed to a predetermined concentration between 3 mol % and 5 mol %;
   a compression molding step of sequentially placing mixtures, obtained in the first material mixing step, the second material mixing step, and the third material mixing step, in a mold for compression molding and performing compression molding; and
   a calcination step of calcining a compression molded product obtained in the compression molding step.

2. The method of claim 1, wherein the organic binder comprises any one selected from the group consisting of polyvinyl alcohol, polyvinyl pyrrolidine, and polyethylene glycol.

3. The method of claim 1, wherein the first material mixing step comprises mixing 93 to 99.9 wt % of the 3 mol % yttrium oxide-tetragonal zirconia polycrystal and 0.1 to 7 wt % of the organic binder.

4. The method of claim 3, wherein the organic binder comprises any one selected from the group consisting of polyvinyl alcohol, polyvinyl pyrrolidine, and polyethylene glycol.

5. The method of claim 1, wherein the second material mixing step comprises mixing 10 to 90 wt % of the 3 mol % yttrium oxide-tetragonal zirconia polycrystal, 3 to 89.9 wt % of the 5 mol % yttrium oxide-tetragonal zirconia polycrystal, and 0.1 to 7 wt % of the organic binder.

6. The method of claim 5, wherein the organic binder comprises any one selected from the group consisting of polyvinyl alcohol, polyvinyl pyrrolidine, and polyethylene glycol.

7. The method of claim 1, wherein the third material mixing step comprises mixing 93 to 99.9 wt % of the 5 mol % yttrium oxide-tetragonal zirconia polycrystal and 0.1 to 7 wt % of the organic binder.

8. The method of claim 7, wherein the organic binder comprises any one selected from the group consisting of polyvinyl alcohol, polyvinyl pyrrolidine, and polyethylene glycol.

9. The method of claim 1, wherein the calcination step comprises placing the compression molded product, obtained in the compression molding step, in an electric furnace and heating the compression molded product to a temperature of 850 to 1050° C.

* * * * *